(12) United States Patent
Ferry

(10) Patent No.: US 8,703,110 B2
(45) Date of Patent: Apr. 22, 2014

(54) COATING SYSTEM

(75) Inventor: Steven J. Ferry, Excelsior, MN (US)

(73) Assignee: Steve Ferry, Excelsior, MN (US)

( * ) Notice: Subject to any disclaimer, the term of this patent is extended or adjusted under 35 U.S.C. 154(b) by 883 days.

(21) Appl. No.: 12/515,894

(22) PCT Filed: Nov. 20, 2007

(86) PCT No.: PCT/US2007/085275
§ 371 (c)(1),
(2), (4) Date: Jan. 19, 2010

(87) PCT Pub. No.: WO2008/064245
PCT Pub. Date: May 29, 2008

(65) Prior Publication Data
US 2010/0143260 A1    Jun. 10, 2010

Related U.S. Application Data

(60) Provisional application No. 60/866,762, filed on Nov. 21, 2006.

(51) Int. Cl.
*A61K 31/74* (2006.01)

(52) U.S. Cl.
USPC ..... 424/78.08; 424/78.37; 424/9.5; 424/9.52; 424/422; 424/423; 424/424; 424/426

(58) Field of Classification Search
None
See application file for complete search history.

(56) References Cited

U.S. PATENT DOCUMENTS

| | | | |
|---|---|---|---|
| 4,399,064 A | 8/1983 | Penneck | |
| 5,746,814 A | 5/1998 | Malhotra et al. | |
| 7,130,107 B2 | 10/2006 | Liu et al. | |
| 2002/0169505 A1 * | 11/2002 | Jethmalani et al. | 623/6.56 |
| 2003/0044451 A1 | 3/2003 | McGhee et al. | |
| 2004/0229971 A1 | 11/2004 | Rossi et al. | |
| 2005/0048124 A1 | 3/2005 | Sarangapani | |
| 2005/0149175 A1 * | 7/2005 | Hunter et al. | 623/1.42 |

FOREIGN PATENT DOCUMENTS

| | | |
|---|---|---|
| WO | WO-2008/064245 A2 | 5/2008 |
| WO | WO-2008/064245 A3 | 5/2008 |
| WO | WO-2008/064245 B1 | 9/2008 |

OTHER PUBLICATIONS

"European Application Serial No. 07868809.0, Extended European Search Report mailed May 20, 2010", 15 pgs.
"Chinese Application Serial No. 200780049180.0, Office Action mailed Jul. 25, 2011", (w/ English Translation), 12 pgs.
"Chinese Application Serial No. 200780049180.0, Response fiied Dec. 9, 2011 to Office Action mailed Jul. 25, 2011", (w/ Engiish Translation of Amended Claims), 10 pgs.
"European Application Serial No.07868809.0, Office Action mailed May 6, 2011", 9 pgs.
"Silicones—vol. 11", *Encyclopedia of Polymer Science and Technology*, Wiiey, Editor, (2003), 765-841.
"European Application Serial No. 07868809.0, Response filed Feb. 29, 2012 to Office Action mailed May 6, 2011", 10 pgs.
"International Application Serial No. PCT/US2007/085275, Written Opinion mailed May 29, 2008", 6 pgs.
"International Application Serial No. PCT/US2007/085275, Search Report mailed May 29, 2008", 4 pgs.

* cited by examiner

*Primary Examiner* — James Rogers
(74) *Attorney, Agent, or Firm* — Schwegman Lundberg & Woessner, P.A.

(57) ABSTRACT

Embodiments of the invention include a system comprising: an Acetoxy curable silicone Binder; and an active agent blended with the silicone binder, effective for one or more of radiopacification, lubricity, elution of a secondary compound such as a drug, echogenic properties, thermal or electrically insulative properties or chemical indicators wherein the silicone binder effectiveness is not substantially changed by the active agent.

4 Claims, No Drawings

COATING SYSTEM

CROSS REFERENCE TO RELATED APPLICATIONS

This application is a U.S. National Stage Filing under 35 U.S.C. 371 From International Patent Application Ser. No. PCT/US2007/085275, Filed Nov. 20, 2007, and published on May 9, 2008 as WO 2008/064245 A2, which claims the benefit of priority of U.S. Provisional Application Ser. No. 60/866,762, filed Nov. 21, 2006. The entire contents of that application are incorporated herein by reference in their entirety.

FIELD

Inventive subject matter described herein relates to a Coating System for providing medical device surfaces, or parts thereof, with a variety of desired performance characteristics which include, but are not limited to, a group of materials that provide for radiopacification, lubricity, elution of a secondary compound such as a drug, echogenic properties, thermal or electrically insulative properties or chemical indicators.

Inventive subject matter employs a Binder material, solvent(s) to thin the Binder if need be and an active agent or agents which can then be applied to various Medical Device surfaces to provide a novel coating which possesses the desired performance attribute without effecting device performance.

BACKGROUND

Some methods of radiopacifying a balloon catheter wherein the balloon has an opacifying layer sandwiched between two other polymeric layers have been described. In addition, coating of the internal lumen of a catheter balloon for radiopacity with the intent being to improve biocompatibility has been attempted. In addition, some methods of compounding opacifyers directly into the base material or chemically altering the polymer to accept a radiopaque moiety into the molecule have been attempted. One problem with compounding has been that the physical characteristics of the base material are often times changed due to the volume of opacifyier required to obtain proper radiopacity. Another prior art method has included assembling precious metal bands onto devices, such as catheters, in order to identify certain locations on the catheter shafts under fluoroscopy.

DESCRIPTION

Although detailed embodiments of the invention are disclosed herein, it is to be understood that the disclosed embodiments are merely exemplary of the invention that may be embodied in various and alternative forms. Specific structural and functional details disclosed herein are not to be interpreted as limiting, but merely as a basis for teaching one skilled in the art to variously employ the system embodiments.

Referred to herein are trade names for materials including, but not limited to, polymers and optional components. The inventor herein does not intend to be limited by materials described and referenced by a certain trade name. Equivalent materials (e.g., those obtained from a different source under a different name or catalog (reference) number to those referenced by trade name may be substituted and utilized in the methods described and claimed herein. All percentages and ratios are calculated by weight unless otherwise indicated.)

All percentages are calculated based on the total composition unless otherwise indicated. All component or composition concentrations are in reference to the active level of that component or composition, and are exclusive of impurities, for example, residual solvents or by-products, which may be present in commercially available sources.

Inventive subject matter described herein employs a Binder with an appropriate opacifier formulated at a specific Wt %, and a solvent, if thinning is required, for application onto the device surface in one or repeated coats until the desired fluoroscopic opacity of the device is achieved. The opacifying coating of embodiments of the invention can be applied to the desired device surface by spraying, sputtering, dipping, brushing, or by other means. Additionally, for some embodiments, the Binder/opacifier can be applied to heat shrinkable tubing that can then be cut to length and reduced over a catheter shaft, providing a lower cost alternative to using precious metal marker bands with equivalent radiopacity.

Lubricious Coatings:

Lubricious coatings include members from a family of Polyvinylpyrolodone (PVP), Polyvinylacetate (PVA), Cellulose Acetates, Paraylene, and others. All of these materials are hydrophilic surface coated materials or in the case of paraylene, which is hydrophobic, used on catheter shafts, guidewire shafts and balloons to provide lubricity to said devices while navigating them intravascularly. These coatings require only a single step or a two-step process; a base material is applied to receive a topcoat or lubricious coat on metal surfaces. These coatings are generally biocompatible. However, there are hydrophobic materials that can provide both lubricity as well as biocompatibility.

Embodiments of the invention allow for formulating a lubricious material, as described above, directly into the Binder, which can then be applied to the desired device surface by spraying, sputtering, dipping, brushing, or by other means.

Eluting Agents:

A large body of work has been done in the prior art relating to the elution of an agent or agents for functional or therapeutic reasons from the surface of a medical device. The majority of these agents are combined within hydrophilic coatings; such as drugs or bioactive agents. The drawback with hydrophilic coatings is that the decay rates are rapid. There are several references to impregnating polymeric materials with eluting agents within the prior art that employ solvents and the eluting agents, which swell materials and flow into the polymer based on a concentration gradient, but not affect the molecular bonds of the substrate material. Once the material has been impregnated with the desired agent, the device is allowed to volatilize the solvent off wherein the eluting agent is trapped within the matrix of the medical device and will remain dormant until hydrolyzed within the body and allowed to elute at various rates, depending on the base material.

Embodiments of the invention allow for mixing the eluting agent directly into the Binder, where upon curing of the Binder, the agent elutes at a slower more controlled rate due to the mechanical and physical properties of the cured Binder. Examples of this application include indicators on therapeutic devices potentially coupled with antibiotics to retard bacterial growth, or antibiotics alone. One such example would be an antibiotic coating on a Foley catheter. Other examples include, but are not limited to, drug coated PIC lines, orthopedic set screws, shunts, and mesh used to repair tears or intra arterial disorders by incorporating bioactive materials or textured materials within the Binder system.

Echogenic Properties:

Ultrasound is a widely accepted diagnostic method to evaluate soft tissue organs, view developing Fetuses, and reconstruct images into 3D display models. Unlike fluoroscopy, which uses lower energy X-ray radiation to generate an image, Ultrasound utilizes sound waves of varying wavelengths and the image is reconstructed based on the echo that is returned from the target area. It is the difference in tissue densities that enable Ultrasound to create an image based on the returning echo signature. The prior art cites several examples of echogenic coatings which are coatings that, when applied, enable the coated surface to be seen. In one embodiment described herein, an echogenic coating used is formed by creating air pockets in a urethane coating to achieve a density difference whereby an image is generated. One issue with this method is lack of durability and compliance. Further, the process of deposing the coating is burdensome and restricted to metal screws.

Embodiments of the invention utilize the Binder with ceramic spheres that are in a range from 5µ-50µ in diameter and contain entrapped air. It is the difference in densities between the ceramic sphere and the air that enables the echo to return to the collector in such a manner that an image is produced.

Thermal and Electrical Insulation:

There is less information relative to medical devices pertaining to coatings that can provide electrical and thermal insulative properties. Ceramic depositions have been cited in the prior art for the coating of metal surfaces requiring insulation, yet ceramic materials are non-compliant and may crack whereby compromising electrical or thermal insulative properties. Also, the cleanliness of the substrate surface is critical for proper insulative adhesion when e-beam or Vapor Deposition methods are employed to apply ceramic coatings to the device surface.

Embodiments of the invention make insulating a desired material substrate much easier by using the Binder material and ensures proper electrical or thermal insulative properties when applied by one of the methods cited based on its physical properties. Additionally, the cured Binder material is compliant, yet well adhered to the substrate.

Chemical Indicators: Chemical indicators are used to identify the presence of microbes or chemical byproducts resulting in distinct color changes due to changes in PH, or other chemical changes. The indicators provide data relative to the presence of a particular molecule, acidity, agent, antigen, antibody and the like. Such indicators are primarily incorporated into a substrate and are not the result of a coating. The prior art has limited information relative to the use of an indicator for the presence of various forms of bacteria on the surface of medical devices such as, but not limited to, PIC Line catheters, Colostomy tubes, Introducers, and the like.

Embodiments of the invention address this need by combining the appropriate indicator with the Binder at the required Wt % and using an appropriate solvent to thin the formulation for application. Further, the chemical indicators could be integrated within the Binder as described above and coated onto an appropriate substrate for placement within open or sealed portions of fresh meat such as beef, fowl, muscles, and fish. If bacteria were present, the package indicator would change colors thereby identifying a bacterial colony which could then be cultured and identified and dealt with prior to consumer contact.

The chemical indicator could also be used for screening for a variety of rather virulent diseases found or passed on in foodstuffs. In addition, each food group could be monitored for the incidence of bacterial contamination prior to reaching the consumer market.

SUMMARY

Embodiments of the invention relate to a versatile system wherein the active agent can be incorporated into a base Binder and applied by methods including, yet not limited to, dipping, spraying, fogging in a chamber, brushing and the like, depending on the geometry of the device.

In addition, curing mechanisms of the Binder may include, but are not limited to, U.V.& RTV curable materials, thermal, chemical and room temperature cures.

The Binder Material Utilized within Embodiments of the Invention

In one embodiment, the Binder material includes a Room Temperature Vulcanization (RTV) silicone elastomer solubilized within an appropriate solvent at a weight percentage of between 1% and 65%, which cures via extraction of moisture from the atmosphere wherein the polymer utilizes the hydroxyl group (OH$^-$) from a water molecule to initiate and complete cross linking of the silane monomer. See FIGS. 1 and 2 below for an example of the curing mechanism.

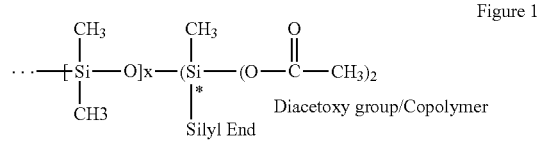

Figure 1

Diacetoxy group/Copolymer Silyl End

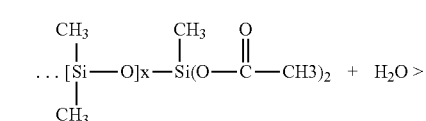

Figure 2

Dimethylsiloxane

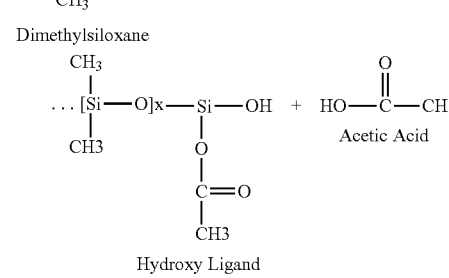

Acetic Acid

Hydroxy Ligand

The curing mechanism includes an acetoxy system in which the chain contains a dimethysiloxane along with a copolymer. See FIG. 1 above. The copolymer contained on the dimethylsiloxane chain contains a methyldiacetoxysilyl group. Curing is achieved by exposure of the elastomer to air. Water particles, or hydroxyl groups (OH), from moisture in the air react to form acetoxy ligans which in turn form free radicals comprised of acidic acid and hydroxy ligands.

It is these acetoxy ligands, which react with other acetoxy ligans on other branches to form Si—O—Si cross-links between polymer chains, with the liberation of acidic acid. A catalyst can be added in order to accelerate the process yet not effect the final outcome. See FIG. 2 above.

In one example illustrating the utility of one embodiment of the present invention, a catheter may be equipped with a compliant expandable balloon. Using one embodiment of the invention, the balloon may be coated on the exterior with a compliant radiopacifying agent, wherein said radiopacifying agent can be Bismuth bicarbonate, Barium Sulfate, Tungsten, Tantalum, Iodides, Borates or other such radiopacifying agents. In one embodiment, the catheter balloon is coated with a radiopacifying agent comprising the (W) or Tungsten radiopacifying agent combined with a Binder, wherein said Binder is a silicone dispersion. In combination with the radiopacifying agent, the Binder material used, such as a polydimethyl siloxane, can be dispersed in an appropriate solvent such as aliphatic hydrocarbons, butylacetate, ethylacetate or THF, all of which are capable of solubilizing elastomeric and polymeric Binder's from a variety of materials such as Silicones, Urethanes, Nitryles, Amides and other polymeric materials which can be dispersed within a solvent and be used as the Binder Agent. These materials, when compounded with a radiopacifying agent can be used to coat a medical device for radiopacity. The materials cited in this example are not exclusively limited to the design, yet are viable to its development.

Citing another example, said (Acetoxy curable silicone Binder material) including a polydimethylsiloxane into which a radiopacifying or other desired agent is combined in an approximate range from 1 Wt % to 60 Wt %. The active agent is suspended within the polydimethylsiloxane, subsequently thinned for application and applied to a guidewire tip, catheter tip, heat shrinkable tubing and the like by methods not limited to dipping, brushing, and spraying, or other such methods. The coating may be applied once or multiple times to achieve the desired performance characteristics. Furthermore, the coating may be applied to medical devices whole or in part, based on the desired characteristics. Portions of the medical device surface may be masked in order to selectively coat the device surface. Further, a sealing agent including a Binder such as polydimethylsiloxane with no active ingredient(s) can be applied to surfaces that will encapsulate the desired agent and aid in biocompatibility. This topcoat may consist of the Binder material without any active ingredients except for the desired solvent to achieve the correct Wt. % ratio of solvent to filler.

The disclosed coating system, once cured, is compliant and capable of adhering to the mechanical requirements of a particular device. A surface primer may also be employed to pre-condition a balloon or other device surface to accept the Binder material and appropriate constituent. Such primers would come from a family of acrylates, urethanes, hydrolytes and amides and the like. In addition to the radiopacifying capability of this embodiment, additional functional materials may be added to the Binder material(s) in order to provide other desired characteristics to a medical device such as lubricity, elution of a desired compound such as a drug, or the use of a chemical indicator for the detection of organisms such as bacteria, bioactive agents, or thermal or electrical insulators.

As an example: The versatility of embodiments of the invention allow for at least a permanently enhanced device which retains its intended physical characteristics yet provides a useful enhancement such as utilizing a chemical indicator for the detection of unwanted microbes on the surface of various medical devices which are percutainously placed and remain indwelling for a terminal period of time.

In this example, a gram positive stain could be formulated with the Binder to form a coating which in the presence of bacteria such as *Staphylococcus, Streptoccus, Clostridium, Bacillus* and *Lysteria* the coating would change color from clear to purple indicating the presence of a bacterial colony reactive with Gram Stain. With said color change, the device can be removed from the patient and a new device placed.

Active Agents:

Within embodiments of the present invention, the Active Agents that are added to the Binder provide the unique characteristic to be achieved on a medical device. Examples include, but are not limited to, radiopacification, lubricity, echogenicity, insulative properties, therapeutic coating, pigments, chemical indicators, and bioactive agents. The agents are formulated into the Binder on a Wt % basis and are mechanically suspended within the matrix of the Binder once the Binder has cured. By design, there is no chemical interaction taking place between the Binder and the Active Agents because chemically altering the active agent could compromise its performance. Once the Binder cures, the Active Agents added to the Binder are encapsulated within the Binder matrix unless the Active Agent is miscible in water, in which case, being porous, the Binder will allow for slow elution of the Active Agent. The speed of elution depends on the concentration or Wt % of Active Agent loaded into the Binder that determines the concentration gradient between the surrounding fluid filled interstitial space and the device coating itself.

Additional Embodiments

The base Binder as described herein and the active ingredients can be applied to a variety if medical grade materials in order to produce a robust low cost means of providing unique performance characteristics to a variety of medical devices. As an example, most current marker bands are made from costly precious metals such as platinum, gold. These metals provide excellent differentiation under fluoroscopy, but increases device costs considerably. Embodiments of the invention enable the user to enjoy the benefits of radiopacity at a lower cost and with comparable resolution by combining an opacifier to the binder to provide proper visualization under flouroscopy.

In yet another embodiment, the coating would utilize an air filled microsphere embedded within the Binder in order to provide a coating capable of allowing medical devices to be visualized under Ultrasound. The reason for sealed air-filled microspheres would be to enhance the return echo from the coated device to the multiple transducers utilized in a 3D ultrasound system. In addition, a non-ferrous material may be used within the Binder to coat the balloons or other devices in lieu of ferrous material for applications in diagnostic instruments such as MRI or CT scanners. Conversely, a magnetic material consisting of the ferrous materials ranging from basic magnetic materials to the more exotic rare earth magnetic materials such as "neodymium iron boron" and the like can be utilized within the Binder system disclosed earlier within this document.

Since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes, which come within the meaning and range of equivalency of the claims, are intended to be embraced therein.

What is claimed is:

1. A coating comprising:
   an acetoxy curable silicone binder comprising ceramic spheres ranging in size from 5 microns to 50 microns, the ceramic spheres containing entrapped air; and a polyvinylpyrrolidone agent blended with the acetoxy curable silicone binder, wherein the acetoxy curable silicone comprises recurring unit of the formula I:

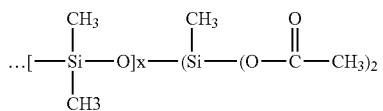
(I)

wherein x is a positive integer.

2. The system of claim 1, wherein the acetoxy curable silicone binder is effective for eluting one or more drugs or bioactive agents or combinations thereof.

3. A medical device comprising:
an acetoxy curable silicone binder; and
a polyvinylpyrrolidone agent blended with the acetoxy curable silicone binder, the acetoxy curable silicone binder comprising sealed, air-filled ceramic microspheres effective for enhancing a return echo from the medical device to tranducers in a 3D ultrasound system, wherein the acetoxy curable silicone comprises recurring unit of the formula I:

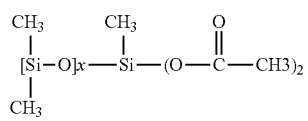
(I)

wherein x is a positive integer.

4. The medical device of claim 3, wherein the medical device is a compliant, expandable balloon.

* * * * *

UNITED STATES PATENT AND TRADEMARK OFFICE
CERTIFICATE OF CORRECTION

| | | |
|---|---|---|
| PATENT NO. | : 8,703,110 B2 | Page 1 of 1 |
| APPLICATION NO. | : 12/515894 | |
| DATED | : April 22, 2014 | |
| INVENTOR(S) | : Steven J. Ferry | |

It is certified that error appears in the above-identified patent and that said Letters Patent is hereby corrected as shown below:

Title page, in column 2, under "Other Publications", line 5, delete "fiied" and insert --filed--, therefor

IN THE CLAIMS:

In column 7, line 7, in Claim 1, delete "(Si" and insert --Si--, therefor

In column 7, line 8, in Claim 1, delete "CH3" and insert --$CH_3$--, therefor

In column 8, line 10, in Claim 3, delete "CH3" and insert --$CH_3$--, therefor

Signed and Sealed this
Twenty-third Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,703,110 B2  
APPLICATION NO. : 12/515894  
DATED : April 22, 2014  
INVENTOR(S) : Steven J. Ferry Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1125 days.

Signed and Sealed this

Twenty-ninth Day of September, 2015

Michelle K. Lee
*Director of the United States Patent and Trademark Office*